United States Patent [19]

Elliott et al.

[11] 4,137,324
[45] Jan. 30, 1979

[54] OPTIONALLY SUBSTITUTED PHENYL-α-CYCLOPROPYL ACETIC ACID ESTERS AND USE AS INSECTICIDES

[75] Inventors: Michael Elliott, Stevenage; Norman F. Janes, Luton; David A. Pulman, Harpenden, all of England

[73] Assignee: National Research Development Corporation, London, England

[21] Appl. No.: 789,226

[22] Filed: Apr. 20, 1977

[30] Foreign Application Priority Data

Apr. 22, 1976 [GB] United Kingdom ............... 16234/76

[51] Int. Cl.² ......................... A01N 9/28; A01N 9/24; A01N 9/20; C07C 121/52
[52] U.S. Cl. ............................... 424/282; 260/326 A; 260/326 N; 260/340.5 R; 260/347.2; 260/347.4; 260/465 D; 424/274; 424/285; 424/304; 424/308; 424/309; 560/21; 560/57; 560/101
[58] Field of Search .................... 260/465 D, 340.5 R; 424/304, 282, 308, 309; 560/21, 57, 101

[56] References Cited

U.S. PATENT DOCUMENTS 3,880,916  4/1975  Dickel et al. ................. 260/465 D X
3,950,535  4/1976  Davis et al. .................. 260/465 D X
4,016,179  4/1977  Fujimoto et al. ............ 260/465 D X

*Primary Examiner*—Richard Raymond
*Attorney, Agent, or Firm*—Murray and Whisenhunt

[57] ABSTRACT

New insecticides are of general formula:

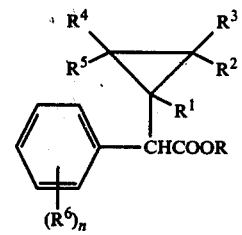

where $R^1$, $R^2$, $R^3$, $R^4$ and $R^5$ represent H or methyl, $R^6$ represents alkyl, alkoxy, halogeno or nitro or two $R^6$ groups together represent methylenedioxy, and R is a group forming insecticidal esters with chrysanthemic acid such as 5-benzyl-3-furylmethyl, 3-phenoxybenzyl or α-cyano-3-phenoxybenzyl. They are prepared by esterification methods.

14 Claims, No Drawings

OPTIONALLY SUBSTITUTED PHENYL-α-CYCLOPROPYL ACETIC ACID ESTERS AND USE AS INSECTICIDES

This invention relates to new esters of certain phenyl acetic acids, useful as insecticides, to processes for their production, to compositions containing them and to the insecticidal use of the compounds and compositions.

It has recently been discovered that insecticidal compounds can be obtained by esterifying certain α-substituted phenyl acetic acids with various alcohols. These known esters include, inter alia, esters in which the second substituent on the α-carbon atom of the phenyl acetic acid can be a cycloaliphatic group but no esters of this type have yet been prepared in which the cycloaliphatic substituent was a cyclopropyl group directly bounded to this α-carbon atom.

We have now developed synthetic methods which have permitted us to prepare new esters of α-cyclopropylphenyl acetic acid which, surprisingly, have been found to possess a combination of physical and chemical properties rendering them valuable as insecticidal compounds.

The present invention provides a compound of the general formula:

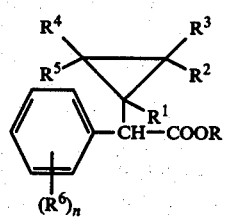

in which $R^1$, $R^2$, $R^3$, $R^4$ and $R^5$, which may be the same or different, each represent hydrogen or a methyl group, $R^6$ represents an alkyl or alkoxy group containing 1 – 4 carbon atoms or a halogeno or nitro group or two groups $R^6$ together represent a methylene dioxy group and n is 0, 1, 2 or 3, the groups $R^6$ being the same or different when n is 2 or 3, and R represents a group of formula:

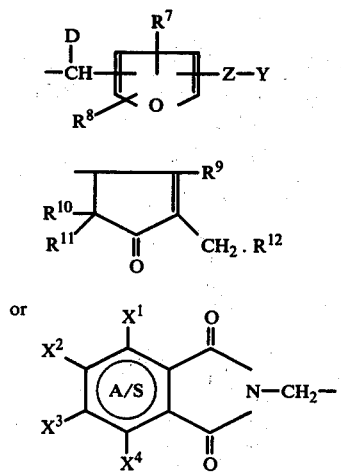

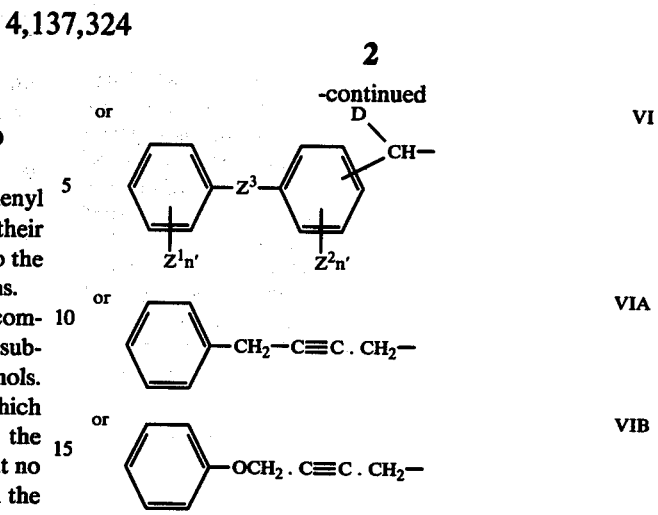

wherein
Z represents O, S, $CH_2$ or CO, Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represent hydrogen or an alkyl, or alkenyl group, $R^9$ represents hydrogen or a methyl group, $R^{10}$ and $R^{11}$, which may be the same or different, each represent hydrogen or an alkyl group, $R^{12}$ represents an organic radical having carbon-carbon unsaturation in a position α to the $CH_2$ group to which $R^{12}$ is attached.

(A/S) indicates an aromatic ring or a dihydro or tetrahydro analogue thereof, $X^1$, $X^2$, $X^3$ and $X^4$, which may be the same or different, each represent hydrogen, chlorine or a methyl group, $Z^3$ represents —$CH_2$— or —O— or —S— or —CO—, D represents H, CN or —C≡CH, $Z^1$ and $Z^2$, which may be the same or different, each represent chlorine or a methyl group and each n', which may be the same or different, is 0, 1 or 2.

In the compounds of the invention, it is preferred that each of $R^1$ to $R^5$ is hydrogen so that the esters are esters of a cyclopropyl acetic acid. It is also preferred that n is o, 1 or 2 and that when n is 1 or 2, an $R^6$ is a methyl fluoro, chloro or bromo group in the para position.

The insecticidal esters of the present invention may be regarded structurally as esters of an α-cyclopropylaryl acetic acid and an alcohol of formula ROH. While the esters may be conveniently described structurally in these terms, it should be appreciated that the esters can be prepared by methods other than esterifying the acid with the alcohol and such alternative methods are normally used in practice.

When the ester is one structurally derived from a furylmethyl alcohol it is preferred that the furylmethyl alcohol be one of the 3-furylmethyl alcohols described in British Patent specification No. 1,168,798. In the furylmethyl alcohols, and particularly in the 3-furylmethyl alcohols, it is preferred that $R^7$ and $R^8$ each represent hydrogen or groups containing up to 4 carbon atoms, particularly a methyl group and that Y represents a phenyl group which is unsubstituted or substituted in the ring by a group containing up to 4 carbon atoms, e.g. methyl or methoxy, or by chlorine, and Z=$CH_2$, 0 or CO— and D=H. Analogues of these compounds where Z=S and D=CN or C≡CH can also be used. Other compounds of interest are those where Y represents a hydrogen atom, an alkyl group containing up to 4 carbon atoms, an alkenyl group containing up to 4 carbon atoms, e.g. vinyl, alkadienyl group containing up to 4 carbon atoms or an alkynyl group e.g. propargyl or a furyl group.

Specific alcohols of this category, from which the esters of the invention are structurally derivable, include 5-benzyl-3-furylmethyl alcohol, 5-benzyl-2-methyl-3-furylmethyl alcohol, 5-benzylfurfuryl alcohol, 4-benzyl-5-methylfurfuryl alcohol, 5-p-xylyl-furfuryl alcohol, 2,4,5-trimethyl-3-furylmethyl alcohol, 4,5-dimethyl-furfuryl alcohol, 5-phenoxy- and 5-benzoyl-3-furylmethyl alcohol and α-cyano and α-ethynyl-5-benzyl-, or -5-benzoyl- pr -5-phenoxy-3-furylmethyl alcohol.

The cyclopentenolones from which the esters of the invention are structurally derivable are those unsubstituted in the 3-position or those substituted in the 3-position by a methyl group, ($R^9$=H or $CH_3$).

The cyclopentenolones unsubstituted in the 3-position are described in British Patent specification No. 1,305,025. Some of these alcohols are the 3-demethyl analogues of the alcohols from which the naturally occurring pyrethrins are derived. In the present invention, it is preferred that $R^{10}$ and $R^{11}$ each represent hydrogen, methyl or ethyl and $R^{12}$ represents an aryl group such as a phenyl group or a phenyl group substituted by a halogeno or alkyl or alkoxy substituent, of 1 to 4 carbon atoms, for example tolyl, xylyl, p-chlorophenyl or p-methoxyphenyl. $R^{12}$ may also represent a 2- or 3-furyl group or an alkenyl group such as a vinyl, prop-1-enyl or buta-1,3-dienyl group.

When the esters of the invention are structurally derivable from the cyclopentenolones which are substituted in the 3-position by the methyl group, ($R^9$=methyl), the esters may be derived from allethrolone ($R^{10}$ = $R^{11}$ = H, $R^{12}$ = vinyl), pyrethrolone ($R^{10}$ = $R^{11}$ = H, $R^{12}$ = buta-1,3-dienyl), cinerolone ($R^{10}$ = $R^{11}$ = H, $R^{12}$ = prop-1-enyl), jasmolone ($R^{10}$ = $R^{11}$ = H, $R^{12}$ = but-1-enyl) or furethrolone ($R^{10}$ = $R^{11}$ = H, $R^{12}$ = 2-furyl).

When the esters of the invention are phthalimidomethyl esters where R is of formula V, they may be phthalimido, dihydrophthalimido or tetrahydrophthalimidomethyl esters where the phthalimido, dihydrophthalimido or tetrahydrophthalimido residue is one described in British Patent specifications Nos. 985,005 and 1,052,119 or 1,052,119 or 1,058,309. 3,4,5,6-Tetrahydrophthalimido-methyl esters are of particular interest.

When the esters of the invention are those where R is of formula VI, it is preferred that they be 3-benzylbenzyl esters, 3-benzoylbenzyl esters or 3-phenoxybenzyl esters although each of the rings may be substituted by up to three chloro and/or methyl groups. Other esters of particular interest where R is of formula VI are those where $Z^3$ represents 0 or $CH_2$ and D represents —CN or C≡CH, e.g. esters of α-cyano- or α-ethynyl-3-phenoxybenzyl alcohol and of α-cyano- or α-ethynyl-3-benzyl- and -3-benzoylbenzyl alcohols.

The compounds of the present invention have at least one site of optical activity and, when the ester where one is D represents cyano or ethynyl, the esters have two sites of optical activity. Furthermore, esters which are substituted in the cyclopropane ring can also exist in the form of geometrical isomers and the present invention includes the individual optical and/or geometrical isomers as well as isomeric mixtures.

The insecticidal esters of the present invention may be prepared by any one of the known esterification methods by reacting a substituted acetic acid or esterifiable derivative thereof of formula II:

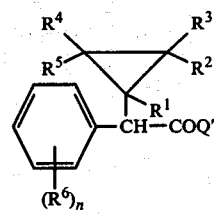

with an alcohol or esterifiable derivative thereof of formula RQ where Q and COQ' are functional groups or atoms which will react together to form an ester linkage and $R^1$, $R^2$, $R^3$, $R^4$, $R^5$ and $R^6$ are as defined above.

It is usually convenient in practice either to react the acid or acid halide with the alcohol ($COQ^1$=COOH or CO-halide and Q=OH) or to react a halogeno compound (Q=halogen) with a salt of the carboxylic acid ($COQ^1$=COO $\ominus$ M $\oplus$ where M is, for example, a silver or triethylammonium cation). Alternatively, a base catalysed trans-esterification can be used by reacting a lower alkyl ester of the aryl acetic acid, where the alkyl group contains 1—3 carbon atoms, with the alcohol ROH.

Certain of the intermediate acids of formula II (Q' = OH) are known compounds but we have developed synthetic mthods which are suitable for producing not only the known substituted acetic acids of formula II but also new substituted acetic acids of formula II. Our synthetic methods are set out below in reaction scheme 1 and reaction scheme 2. These reaction schemes show the synthesis of α-cyclopropyl-phenyl acetic acid but by using appropriately substituted starting materials, α-cyclopropyl phenyl acetic acids substituted in one or both of the rings can be obtained by analogous methods.

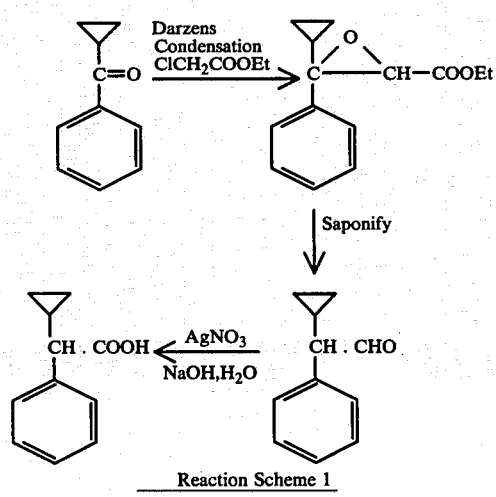

Reaction Scheme 1

-continued

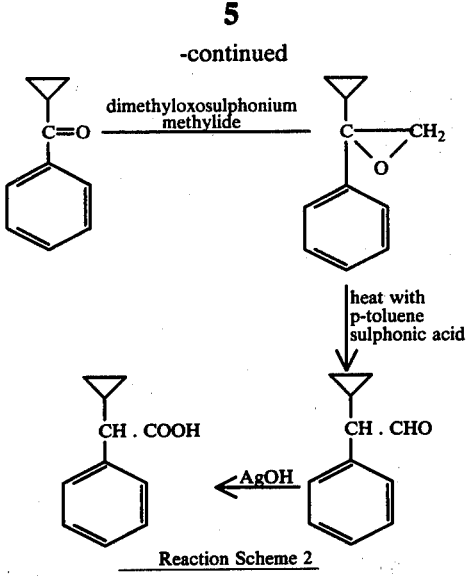

Reaction Scheme 2

Both syntheses start from cyclopropyl phenyl ketone which is an available intermediate. This intermediate may itself be prepared by reacting benzene with γ-chlorobutyryl chloride under the conditions of the Friedel-Crafts reaction to form an acyclic ketone of formula $C_6H_5COCH_2CH_2CH_2Cl$ which is then dehydrohalogenated by treatment with alkali to form the cyclopropyl phenyl ketone.

In reaction scheme 1, the ketone is first reacted with ethyl chloroacetate under the conditions of the Darzens reaction in the presence of a strong base, for example potassium tertiary butoxide in tertiary butanol. The resulting stable oxirane intermediate is then saponified with base to give an unstable intermediate acid which rearranges, with loss of carbon dioxide, to form an α-cyclopropyl-phenyl acetaldehyde. This aldehyde is subsequently oxidised with a reagent known to be suitable for oxidising aldehyde groups to acids groups, for example moist silver oxide.

Reaction scheme 2 starts from the same cyclopropyl phenyl ketone but in the first step of the reaction, the ketone is reacted with dimethyloxosulphonium methylide, for example in dimethylsulphoxide for about 24 hours. The reagent used is an ylide of formula $(CH_3)_2S^+O-C^{-H}_2$ which is obtainable by reacting dimethyl sulphoxide with methyl iodide to form a quaternary iodide and reacting the quaternary iodide with sodium hydride. The reaction with the ylide forms a stable oxirane intermediate which rearranges under the influence of heat and acid, for example by heating in benzene with p-toluene sulphonic acid or boron trifluoride etherate to form α-cyclopropyl-phenylacetaldehyde which can be oxidised to the corresponding acetic acid by a similar method to that described above.

An alternative synthesis of the intermediate aldehyde starting from the aryl cyclopropyl ketone is shown in scheme 3.

Reaction Scheme 3.

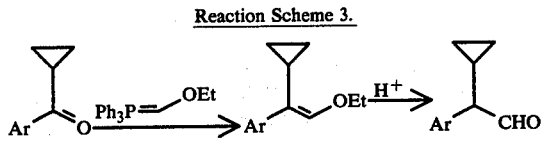

One or more of the insecticidal esters of the invention may be formulated with an inert carrier or diluent to give insecticidal compositions and these may be prepared, for example, in the form of dusts and granular solids, wettable powders, mosquito coils and other solid preparations or as emulsions, emulsifiable concentrates, sprays and aerosols and other liquid preparations after the addition of the appropriate solvents, diluents and surface active agents.

Synergists such as piperonyl butoxide or tropital, may be added to these compositions. Certain insecticidal esters of the invention show superiority over pyrethrin like esters in the ability to respond to synergists and many esters of the invention have a valuable synergistic factor.

The insecticidal compositions may also include synthetic pyrethrins to improve kill and/or knock down or to synergise the activity of the insecticides of this invention.

The new esters of the invention or insecticidal compositions containing them may be used for killing insects or controlling the level of insects on a domestic or agricultural scale by reacting the insects themselves or an environment susceptible to insect attack with the compounds or compositions.

The following Examples are given to illustrate the invention.

EXAMPLE 1

5-Benzyl-3-furylmethyl-α-cyclopropyl-p-chlorophenyl acetate (a) p-Chlorophenyl cyclopropyl ketone A mixture of anhydrous aluminium chloride (20 g) and chlorobenzene (100 ml) was cooled to 10–15° C and treated dropwise with a solution of 4-chlorobutyryl-chloride (20 g) in chlorobenzene (20 ml) over a period of 10 minutes with continuous stirring. The solution was warmed to 20–25° C and stirring was continued for a further 1 hour. It was poured onto ice and extracted with ether and the dried ethereal extract evaporated. The resulting liquid was treated with a solution of potassium hydroxide (12 g) in methanol (60 ml) and left to stand for 30 minutes with occasional shaking. After filtration the residue was washed with methanol and the filtrate evaporated to dryness. The oil was dissolved in ether and washed with water. The dried ethereal solution ($Na_2SO_4$) was evaporated and distilled (b.p.125–127°/5mm), yield=21.3 g, $n_D$= 1.5700

Ethyl β-cyclopropyl-β-p-chlorophenyl glycidate

A solution of potassium (3.4g) in dry t-butanol (80 ml) was added slowly to a solution of ethyl chloroacetate (9.8g) and p-chlorophenyl cyclopropyl ketone (9.0 g) in benzene (25 ml) and dry t-butanol (10 ml) kept at 5–10° C under nitrogen with stirring. The solution was left to stir at room temperature for 21 hours and water added. The product was extracted with ether and the ethereal solution was washed with saturated NaCl, dried, evaporated, and distilled (b.p. 140-147°/1mm), (10.2g), $n_D$=1.5120.

(c) α-Cyclopropyl-p-chlorophenyl acetaldehyde

The glycidic ester from (b) above (10.2g) and potassium hydroxide (11g) dissolved in ethanol (100 ml) and water (0.5ml) were stirred at room temperature for 20 hours. The solvent was removed "in vacuo" and dilute hydrochloric acid added. The product was extracted into ether, washed with saturated NaCl, dried and evaporated. (b.p. 120–126° C /1mm., 4.5 g), $n_D$=1.5480.

(d) α-Cyclopropyl-p-chlorophenylacetic acid

The aldehyde from (c) above (2.25g) in ethanol (0.5ml) was added to a mixture of silver nitrate (2.68) and sodium hydroxide (1.6g) in water (17ml). The mixture was stirred at room temperature for 17 hours then filtered and the residue washed with water and ethanol. Acidification with dilute hydrochloric acid yielded the product which was extracted into ether, dried and evaporated. Yield = 2.33g (semi solid).

(e) 5-Benzyl-3-furylmethyl Ester

The acid from (d) above (210mg) dissolved in dry benzene (5ml) was treated successively with pyridine (100μl) ) and thionyl chloride (75 μl) and left to stand for 3 hours. The resulting acid chloride was treated with a solution of 5-benzyl-3-furylmethyl alcohol (200 mg) and pyridine (100 μl) in benzene (5 ml) and left to stand overnight. Chromatography on neutral alumina eluting with benzene gave, after evaporation, 5-benzyl-3-furylmethyl α-cyclopropyl p-chlorophenyl acetate (230 mg) $n_D$ 1.5655.

EXAMPLE 2

5-Benzyl-3-furylmethyl α-cyclopropyl-p-chlorophenyl acetate was prepared by a procedure similar to that described in Example 1 except that the α-cyclopropyl-p-chlorophenyl acetaldehyde was prepared by the following procedure:

(a) 1-Cyclopropyl-1-p-chlorophenyl oxirane

80% Sodium hydride (0.5 g) was added to a solution of trimethyloxosulphonium iodide (2.8 g) in dry dimethylsulphoxide (25ml) with stirring, under nitrogen. The yellow solution was stirred for 2 hours at room temperature when a solution of p-chlorophenyl cyclopropyl ketone prepared as described in Example 1(a) (2.0 g) in dry dimethylsulphoxide (5ml) was added. After leaving to stir overnight under these conditions water was added and the product extracted into ether, washed with water, saturated NaCl, dried ($Na_2SO_4$) and evaporated. Yield=2.35 g. $n_D$=1.5512.

(b) α-Cyclopropyl-p-chlorophenylacetaldehyde

The crude oxirane prepared above (2.23g) was isomerised by distillation from p-toluenesulphonic acid (70 mg). The product had b.p. 80–90/0.5 mm, yield=0.82g, $n_D$1.5562.

EXAMPLE 3

The procedure of Example 1 was repeated but replacing the 5-benzyl-3-furylmethyl alcohol by 3-phenoxybenzyl alcohol or α-cyano-3-phenoxybenzyl alcohol to give the corresponding esters.

EXAMPLE 4

The procedure of Examples 1 and 3 was repeated but replacing the acid by α-cyclopropyl-p-bromophenylacetic acids prepared from the bromophenyl cyclopropyl ketone.

EXAMPLE 5

The procedure of Examples 1 and 3 was repeated but replacing the acid by α-cyclopropyl-p-tolyl-acetic acid prepared from the tolyl cyclopropyl ketone.

EXAMPLE 6

The procedure of Examples 1 and 3 was repeated but replacing the acid by α-cyclopropyl-3,4-dimethylphenyl acetic acid prepared from the dimethylphenyl cyclopropyl ketone.

EXAMPLE 7

The procedure of Examples 1 and 3 was repeated but replacing the acid by α-(2-methyl-cyclopropyl)-p-chlorophenyl acetic acid prepared from the chlorophenyl methylcyclopropyl ketone.

EXAMPLE 8

The procedure of Examples 1 and 3 was repeated but replacing the acid by α-cyclopropyl-p-ethylphenylacetic acid prepared from the ethylphenyl cyclopropyl ketone.

EXAMPLE 9

The procedure of Examples 1 and 3 was repeated but replacing the acid by α-cyclopropyl-p-fluorophenylacetic acid prepared from the fluorophenyl cyclopropyl ketone.

EXAMPLE 10

The procedure of Example 3 was repeated but replacing the acid by α-cyclopropyl-3,4-methylenedioxy phenyl acetic acid prepared from the methylenedioxyphenyl cyclopropyl ketone.

EXAMPLE 11

α-Cyclopropyl-p-bromophenyl acetic acid, prepared as described in Example 4, was resolved into its individual optical isomers using optically active phenylethylamine. Salts was formed from the racemic acid and (−)-phenyl-ethylamine and recrystallised 4 times from 60% v/v aqueous ethanol when the less soluble salt of the (+)-acid was recovered. A similar procedure was used with (+-phenylethylamine to give the salt of the (−)-acid and the (+)-acid and (−)-acid were then esterified as described in Examples 1 and 3 to give optically active esters. The ester prepared with α-cyano-3-phenoxy benzyl alcohol is itself a mixture of isomers of the (+) and (−) forms of the alcohol.

The refractive index of each of the esters prepared as described in Examples 1–11 is given in the relative toxicity table below.

The insecticidal activity of the esters of the invention was assessed against houseflies and mustard beetles using the following techniques.

Houseflies (*Musca domestica*).

Female flies were treated on the thorax with a one microliter drop of insecticide dissolved in acetone. Two replicates of 15 flies were used at each dose rate and 6 dose rates were used per compound under test. After treatment, the flies were maintained at a temperature of 20° C.±1° and kill was assessed 24 and 48 hours after treatment. $LD_{50}$ values were calculated in micrograms of insecticides per fly and relative toxicities were calculated from the inverse ratios of the $LD_{50}$ values (see Sawicki et al, Bulletin of the World Health Organisation, 35,893, (1966) and Sawicki et al, Entomologia and Exp. Appl. 10, 253, (1967).

Mustard Beetles (*Phaedon cochleariae* Fab)

Acetone solutions of the test compound were applied ventrally to adult mustard beetles using a micro drop applicator. The treated insects were maintained for 48 hours after which time kill was assessed. Two replicates of 40 to 50 mustard beetles were used at each does level and 3 to 4 dose levels were used for each compound. Again, $LD_{50}$ values were calculated and relative toxicities were calculated from the inverse ratios of $LD_{50}$ (see Elliott et al., J. Sci. Food Agric. 20, 561 (1969).

Relative toxicities were calculated by comparison with 5-benzyl-3-furyl-methyl (+)-trans-chrysanthemate (bioresmethrin) which is one of the most toxic chrysanthemate esters known to houseflies and mustard beetles, its toxicity being about 24 times that of allethrin to houseflies and 65 times that of allethrin to mustard beetles and whose toxicity is taken as 1000 against each species is the following table:

The Table below lists the esters prepared and gives their refractive index and relative toxicity. 5B3F indicates 5-benzyl-3-furyl methyl, 3POB indicates 3-phenoxy-benzyl and α-CN-3POB indicates α-cyano-3-phenoxybenzyl.

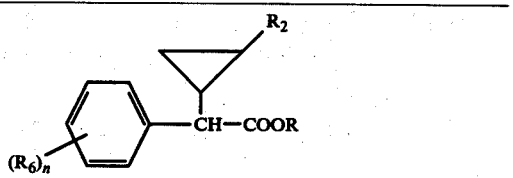

| Example No. | $R_6$ | $R_2$ | $R_5$ | $n_{20}^D$ | Relative Toxicity Bioresmethrin = 1000 | |
|---|---|---|---|---|---|---|
| | | | | | Houseflies. | Mustard Beetles. |
| 1 and 2 | p-Cl | H | 5B3F | 1.5655 | 530 | 170 |
| 3 | p-Cl | H | 3POB | 1.5804 | 320 | 200 |
| 3 | p-Cl | H | α-CN-3POB | 1.5710 | 480 | 570 |
| 4 | p-Br | H | 5B3F | 1.5720 | 220 | 180 |
| 4 | p-Br | H | 3POB | 1.5890 | 260 | 230 |
| 4 | p-Br | H | α-CN-3POB | 1.5814 | 270 | 610 |
| 5 | p-Me | H | 5B3F | 1.5552 | 220 | 76 |
| 5 | p-Me | H | 3POB | 1.5692 | 180 | 250 |
| 5 | p-Me | H | α-CN-3POB | 1.5600 | 270 | 500 |
| 6 | 3,4-Me$_2$ | H | 5B3F | 1.5530 | 230 | — |
| 6 | 3,4-Me$_2$ | H | 3POB | 1.5668 | 130 | — |
| 6 | 3,4-Me$_2$ | H | α-CN-3POB | 1.5622 | 200 | 92 |
| 7 | p-Cl | Me | 5B3F | 1.5563 | 26 | 9 |
| 7 | p-Cl | Me | 3POB | 1.5736 | 28 | 18 |
| 7 | p-Cl | Me | α-CN-3POB | 1.5699 | 65 | 110 |
| 8 | p-C$_2$H$_5$ | H | 5B3F | 1.5551 | 260 | 10 |
| 8 | p-C$_2$H$_5$ | H | 3POB | 1.5728 | 140 | 50 |
| 8 | p-C$_2$H$_5$ | H | α-CN-3POB | 1.5667 | 200 | 50 |
| 9 | p-F | H | 5B3F | 1.5491 | 110 | 100 |
| 9 | p-F | H | 3POB | 1.5678 | 110 | 100 |
| 9 | p-F | H | α-CN-3POB | 1.5628 | 100 | 500 |
| 10 | 3,4-methylene dioxy | H | 3POB | 1.5830 | 80 | 200 |
| 10 | 3,4-methylene dioxy | H | α-CN-3POB | 1.5730 | 60 | 400 |
| 11 | (+)-p-Br | H | 5B3F | m.p.37–9° C. | 450 | 1100 |
| 11 | (+)-p-Br | H | 3POB | 1.5923 | 350 | 520 |
| 11 | (+)-p-Br | H | α-CN-3POB | 1.5840 | 480 | 1600 |
| 11 | (−)-p-Br | H | 5B3F | m.p.39–40° C | 14 | 35 |
| 11 | (−)-p-Br | H | 3POB | 1.5892 | 44 | 67 |
| 11 | (−)-p-Br | H | α-CN-3POB | 1.5829 | 18 | 84 |

Compounds of the invention have also been found to exhibit significant toxicity towards lepidopterous pests and to exhibit a satisfactorily low mammalian and fish toxicity.

We claim:
1. A compound of the general formula

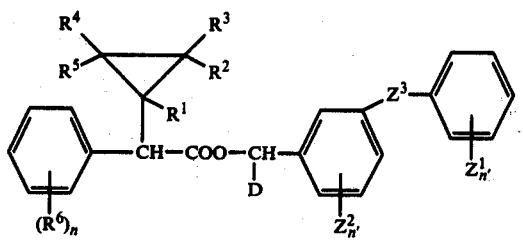

in which $R^1$, $R^2$, $R^3$, $R^4$ and $R^5$, which may be the same or different, each represent hydrogen or a methyl group, $R^6$ represents an alkyl or alkoxy group containing 1 to 4 carbon atoms or a halogeno or nitro group or two groups $R^6$ together represent a methylenedioxy group and n is 0, 1, 2 or 3, the groups $R^6$ being the same or different when n is 2 or 3, D is H or CN, $Z^3$ represents $CH_2$, O, S or CO, $Z^1$ and $Z^2$, which may be the same or different, each represent chlorine or a methyl group and each n', which may be the same or different is 0, 1 or 2.

2. A compound according to claim 1 wherein D is H.
3. A compound of the general formula:

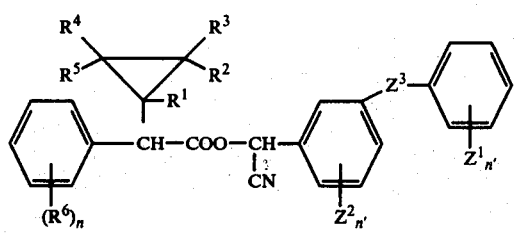

in which $R^1$, $R^2$, $R^3$, $R^4$ and $R^5$, which may be the same or different, each represent hydrogen or a methyl group, $R^6$ represents an alkyl or alkoxy group containing 1 to 4 carbon atoms or a halogeno or nitro group or two groups $R^6$ together represent a methylenedioxy group and n is 0, 1, 2 or 3, the groups $R^6$ being the same or different when n is 2 or 3, $Z^3$ represents $CH_2$, O, S or CO, $Z^1$ and $Z^2$, which may be the same or different, each represent chlorine or a methyl group and each n', which may be the same or different, is 0, 1 or 2.

4. A compound according to claim 3, wherein $R^1$, $R^2$, $R^3$, $R^4$ and $R^5$ represents hydrogen.

5. A compound according to claim 3, wherein n = 1 and $R^6$ is in the para position.

6. A compound according to claim 5 wherein $R^6$ is a fluoro chloro or bromo group.

7. A compound according to claim 3, wherein R represents an α-cyano-3-phenoxybenzyl group.

8. A compound according to claim 2 which is 3-phenoxybenzyl-4-chlorophenyl-α-cyclopropyl-acetate or 3-phenoxybenzyl-4-bromophenyl-α-cyclopropyl-acetate.

9. The compound according to claim 3 which is (±)-α-cyano-3-phenoxybenzyl (±)-4-chlorophenyl-α-cyclopropylacetate.

10. The compound according to claim 3 which is (±)-α-cyano-3-phenoxybenzyl (+)-4-bromophenyl-α-cyclopropyl acetate.

11. An insecticidal composition comprising an insecticidally effective amount of a compound according to claim 2, together with an inert carrier or diluent.

12. An insecticidal composition comprising an insecticidally effective amount of a compound according to claim 3 together with an inert carrier or diluent.

13. A method of insect control which comprises applying to an insect or to an environment susceptible to insect attack, an insecticidally effective amount of a compound according to claim 2.

14. A method of insect control which comprises applying to an insect or to an environment susceptible to insect attack an insecticidally effective amount of a compound according to claim 3.

* * * * *